(12) United States Patent
Sakamoto et al.

(10) Patent No.: US 8,716,762 B2
(45) Date of Patent: May 6, 2014

(54) BIOSENSOR KIT

(75) Inventors: Mitsuru Sakamoto, Tokyo (JP);
Hirohiko Urushiyama, Tokyo (JP);
Hiroaki Kikuchi, Tokyo (JP); Tomoaki Yamabayashi, Tokyo (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 0 days.

(21) Appl. No.: 13/635,125

(22) PCT Filed: Mar. 15, 2011

(86) PCT No.: PCT/JP2011/001495
§ 371 (c)(1),
(2), (4) Date: Sep. 14, 2012

(87) PCT Pub. No.: WO2011/114705
PCT Pub. Date: Sep. 22, 2011

(65) Prior Publication Data
US 2013/0028789 A1    Jan. 31, 2013

(30) Foreign Application Priority Data
Mar. 19, 2010   (JP) ................. 2010-064676

(51) Int. Cl.
*G01N 27/414*   (2006.01)
*H01L 23/26*    (2006.01)

(52) U.S. Cl.
USPC ........... 257/252; 257/253; 257/414; 257/678; 257/682; 435/287.1; 435/287.2; 435/287.7; 435/287.9; 435/288.3

(58) Field of Classification Search
USPC ........ 435/6, 7; 257/414, 428, 253; 438/48, 49
See application file for complete search history.

(56) References Cited

U.S. PATENT DOCUMENTS

| 2003/0088239 A1 | 5/2003 | Takaki et al. |
| 2006/0205013 A1 | 9/2006 | Shim et al. |

(Continued)

FOREIGN PATENT DOCUMENTS

| JP | 06-229970 A | 8/1994 |
| JP | 11-271260 A | 10/1999 |

(Continued)

OTHER PUBLICATIONS

Gilchrist et al., General purpose, field-portable cell-based biosensor platform Biosensors and Bioelectronics, vol. 16, Issues 7-8, Sep. 2001, pp. 557-564.*

(Continued)

*Primary Examiner* — Paul Hyun
*Assistant Examiner* — Robert Eom
(74) *Attorney, Agent, or Firm* — Washida & Associate

(57) ABSTRACT

Disclosed are: a biosensor kit in which a bionsensor utilizing a field effect transistor is not deteriorated during storage or transport; and a system for detecting a substance of interest, which is equipped with the biosensor chip. The biosensor kit comprises a biosensor chip which can measure a substance of interest quantitatively and a package which can hermetically seal the biosensor chip and is composed of a packaging material comprising a metal film. The biosensor chip can measure the substance quantitatively based on the value of a current generated in a field effect transistor when the substance is reacted with a molecule that can recognize the substance and is immobilized on a reaction field connected to the field effect transistor. The biosensor chip comprises the field effect transistor and a mounting substrate on which the field effect transistor is mounted.

5 Claims, 10 Drawing Sheets

(56) References Cited

U.S. PATENT DOCUMENTS

| | | | |
|---|---|---|---|
| 2008/0283875 A1* | 11/2008 | Mukasa et al. | ................ 257/253 |
| 2009/0153130 A1 | 6/2009 | Shim et al. | |
| 2011/0042673 A1 | 2/2011 | Yamabayashi et al. | |

FOREIGN PATENT DOCUMENTS

| JP | 2001-181597 A | 7/2001 |
|---|---|---|
| JP | 2004-085392 A | 3/2004 |
| JP | 2006-201178 A | 8/2006 |
| JP | 2007-139762 A | 6/2007 |
| JP | 2008-082988 A | 4/2008 |
| JP | 2008-134255 A | 6/2008 |
| WO | 2009/122590 A1 | 10/2009 |
| WO | 2009/144878 A1 | 12/2009 |

OTHER PUBLICATIONS

Kamahori et al., Detection of DNA hybridization and extension reactions by an extended-gate field-effect transistor: Characterizations of immobilized DNA-probes and role of applying a superimposed high-frequency voltage onto a reference electrode, Biosensors and Bioelectronics, vol. 23, Issue 7, Feb. 28, 2008, pp. 1046-1054.*

Shishkin et al., Immunological biochips for parallel detection of surface antigens and morphological analysis of cells, Biochemistry (Moscow) Supplement Series A: Membrane and Cell Biology, Sep. 2008, vol. 2, Issue 3, pp. 225-230.*

* cited by examiner

BIOSENSOR KIT

TECHNICAL FIELD

The present invention relates to a biosensor kit which has a biosensor chip.

BACKGROUND ART

Biosensors which use a field-effect transistor (FET) have been proposed (see Patent Literatures 1 to 3). Generally, field-effect transistor-based biosensors include a field-effect transistor and a reaction field for a detection target, which is formed over a channel. The reaction field is provided with a reaction film with which the detection target is bound. The biosensor applies a gate voltage to the field-effect transistor by a gate electrode from above the reaction film, and measures a source-drain current at this time to determine the presence or absence, concentration etc. of the detection target, which has been provided on the reaction field. The FET-based biosensors exhibit very high sensitivity, and therefore there has been growing expectations for practical use.

CITATION LIST

Patent Literature

PTL 1 Japanese Patent Application Laid-Open No. 2004-85392
PTL 2 Japanese Patent Application Laid-Open No. 2006-201178
PTL 3 Japanese Patent Application Laid-Open No. 2007-139762

SUMMARY OF INVENTION

Technical Problem

Despite such growing expectations for use as high-sensitivity sensors, the FET-based biosensors suffer from the drawback of a large variation in sensitivity depending on the service condition. Sensitivity variation occurs depending not only on the environment in which measurement is done by the biosensor, but also on the storage condition for the biosensor.

For instance, when the biosensor in storage is exposed to humidity, a channel (especially carbon nanotube channel) of the field-effect transistor may degrade, and hysteresis or the like may occur. When the biosensor in storage is exposed to light, the light infiltrates into the semiconductor substrate of the FET and the characteristics may be changed. Alternatively, when target recognition molecules are immobilized on a reaction field, the molecules may degrade during storage of the biosensor to cause sensitivity reduction.

An object of the present invention is therefore to provide means of preventing deterioration of a PET-based biosensor during storage or transportation. Thereby, commercialization of FET-based biosensors is achieved.

Solution to Problem

A first aspect of the present invention relates to a biosensor kit given below.

[1] A biosensor kit including:
a biosensor chip for measuring a value of an electric current in a field-effect transistor, the electric current generated when a detection target is allowed to react with a target recognition molecule immobilized onto a reaction field connected to the field-effect transistor; and
a packing body which seals therein the biosensor chip, the packaging body being formed from a packing material having a metal film, wherein
the biosensor chip has the field-effect transistor and a mounting board having thereon the field-effect transistor,
the field-effect transistor comprises: a semiconductor substrate having an insulating film on a surface thereof; a source electrode and a drain electrode, the source electrode and the drain electrode being arranged on the insulating film; a channel formed of a semiconductor, the channel being arranged on the insulating film and being electrically connected to the source electrode and the drain electrode; and the reaction field formed on the semiconductor substrate, the reaction field for supplying a gate potential to the field-effect transistor, and
the mounting board includes thereon external connection terminals electrically connected to the source electrode, the drain electrode and the reaction field, respectively.

[2] The biosensor kit according to [1], wherein the biosensor kit further comprises the target recognition molecule enclosed in the packing body, wherein the target recognition molecule is packed separately from the biosensor chip.

[3] The biosensor kit according to [2], wherein the reaction field has been subjected to surface treatment for immobilizing the target recognition molecule onto the reaction field.

[4] The biosensor kit according to [3], wherein the surface treatment for the reaction field is silanizing treatment.

[5] The biosensor kit according to [3], wherein the surface treatment for the reaction field is a treatment in which a thin film of gold or platinum is formed on the reaction field and an SAM film is formed on the thin film.

[6] The biosensor kit according to [1], wherein the target recognition molecule is immobilized on the reaction field.

[7] The biosensor kit according to [6], wherein the reaction field is moisturized by a moisturizing member.

[8] The biosensor kit according to any one of [1] to [7], further including a desiccating agent or a moisture absorbent enclosed in the packing body.

[9] The biosensor kit according to any one of [1] to [8], wherein the channel is formed from a carbon nanotube, polysilicon or amorphous silicon.

[10] The biosensor kit according to any one of [1] to [9], wherein the insulating film is a silicon nitride film, a silicon oxide film or a hafnium oxide film.

A second aspect of the present invention relates to a biosensor kit given below.

[11] A biosensor kit including:
a biosensor chip for measuring a value of an electric current in a field-effect transistor, the electric current generated when a detection target is allowed to react with a target recognition molecule immobilized onto a reaction field and the reaction field is connected to the field-effect transistor; and
a packing body which seals therein the biosensor chip, the packaging body being formed from a packing material having a metal film, wherein
the biosensor chip has a mounting board and the reaction field formed on the mounting board,
the mounting board includes an external connection terminal for applying a predetermined potential to the reaction field, and an external connection terminal for supplying a potential generated in the reaction field as a gate potential of the field-effect transistor.

[12] The biosensor kit according to [11], further including the target recognition molecule enclosed in the packing body, wherein the target recognition molecule is packed separately from the biosensor chip.

[13] The biosensor kit according to [11] or [12], wherein the reaction field has been subjected to surface treatment for immobilizing the target recognition molecule onto the reaction field.

[14] The biosensor kit according to [13], wherein the surface treatment for the reaction field is silanizing treatment.

[15] The biosensor kit according to [13], wherein the surface treatment for the reaction field is a treatment in which a thin film of gold or platinum is formed on the reaction field and an SAM film is formed on the thin film.

[16] The biosensor kit according to [11], wherein the target recognition molecule is immobilized on the reaction field.

[17] The biosensor kit according to [16], wherein the reaction field is moisturized by a moisturizing member.

[18] The biosensor kit according to any one of [11] to [17], wherein the reaction field is formed on a semiconductor substrate arranged on the mounting board.

[19] The biosensor kit according to any one of [11] to [17], wherein the mounting board is made from an inorganic material, an organic material or a mixed material thereof.

Advantageous Effects Of Invention

According to the biosensor kit of the present invention, the characteristics of the field-effect transistor provided in the biosensor chip are hard to change during storage or transportation of the biosensor kit, and accordingly stable biosensing can be achieved.

DESCRIPTION OF EMBODIMENTS

Biosensor Kit

Figure 1A:
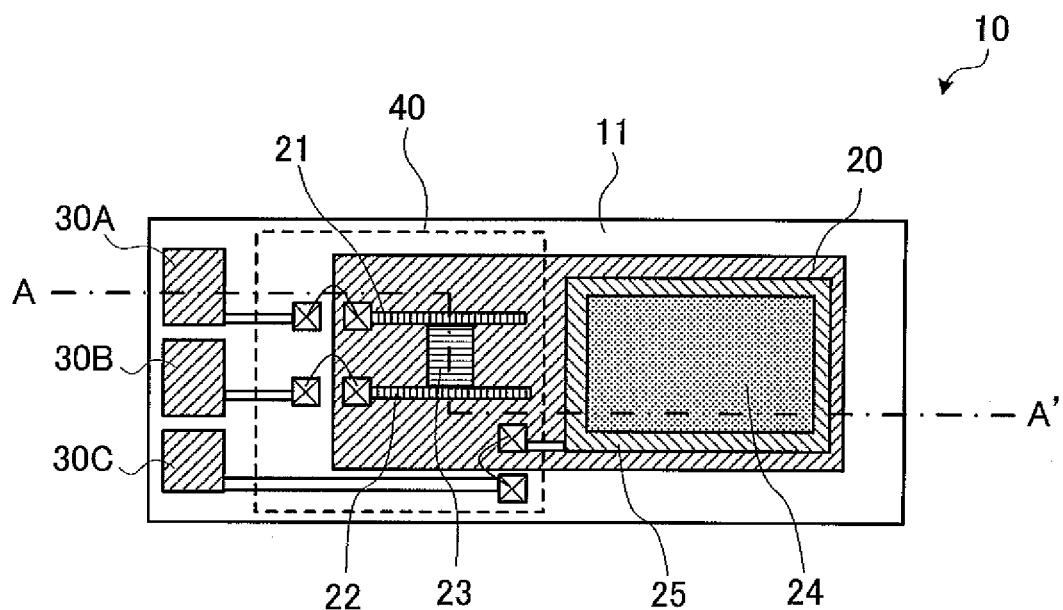
FIG. 1A is a plan view of a first example of a biosensor chip of a first form.

A biosensor kit of the present invention has a biosensor chip and a packing body which seals therein the biosensor chip. The packing body for sealing therein the biosensor chip is preferably a laminated film having a metal film. This is to effectively prevent the possible permeation of moisture and penetration of light from the outside to the inside. The packing body has, for instance, a heat-fusible resin layer as the inner layer of a film constituting the packing body, and the opening of the packing body is closed by fusion.

In the packing body, a desiccating agent or a moisture absorbent may be sealed together with the biosensor chip. This is because if the biosensor chip has been exposed to moisture, the chip tends to easily deteriorate. In addition, elements to be used in the sensing step may also be enclosed in the packing body, e.g., a washer for washing a reaction field, and a remover for removing a washing liquid from the reaction field after washing.

The biosensor chip included in the biosensor kit of the present invention is classified into two forms depending on whether the biosensor chip includes a field-effect transistor element. The biosensor chip of the first form has a field-effect transistor and a mounting board on which the field-effect transistor is mounted. On the other hand, the biosensor chip of the second form has the mounting board and the reaction field formed on the mounting board, but does not have a field-effect transistor structure.

Detection System for Detection Target

A detection system for the detection target of the present invention includes a biosensor chip and a detection device. The biosensor chip may be biosensor chip of either of the first and second forms. The detection system for the detection target, which is provided with the biosensor chip of the second form, free from a field-effect transistor, employs a detection device including the field-effect transistor. The detection device may also include elements to be used in the sensing step, e.g., a washer for washing a reaction field, and a remover for removing a washing liquid from the reaction field after washing.

The biosensor chip of the first form and the biosensor chip of the second form will be each described below.

Biosensor Chip of First Form

The biosensor chip of the first form has a field-effect transistor and a mounting board. The field-effect transistor has a semiconductor substrate having an insulating film thereon, a source electrode and a drain electrode which are arranged on the insulating film, and a channel formed of a semiconductor which is arranged on the a insulating film and is electrically connected to the source electrode and the drain electrode.

The semiconductor substrate of the field-effect transistor is usually a silicon substrate, but is not necessarily limited thereto, and may be an SOI substrate, a compound semiconductor substrate or a glass substrate. The source/drain electrodes and the channel are arranged on the surface of the semiconductor substrate, with the insulating film being formed on the surface on which the components are arranged. The insulating film is not limited in particular, and is appropriately selected according, for example, to the type of the channel; it can be a silicon oxide film, a silicon nitride film or a hafnium oxide film.

The material of the source electrode and the drain electrode may be a conductive material such as a metal or semiconductor material, and is not limited in particular. The channel which connects the source electrode and the drain electrode may be made of semiconductor, and can be a carbon nanotube, a polysilicon film or an amorphous silicon film. When the channel is formed from a carbon nanotube, the insulating film on the surface of the semiconductor substrate may be preferably a silicon nitride film or a hafnium oxide film. On the other hand, when the channel is formed from polysilicon or amorphous silicon, the insulating film on the surface of the semiconductor substrate may be preferably a silicon oxide film or a hafnium oxide film.

It is preferable that the source electrode, the drain electrode and the channel are sealed so as not to come in contact with moisture or not to be exposed with light. When moisture comes in contact with the channel or the channel is exposed with light, the characteristics of the field-effect transistor may remarkably change, which may result in failure to conduct proper detection. In particular, when the channel is formed from polysilicon or amorphous silicon, the channel tends to be easily affected by light. The sealing may be accomplished by covering the source electrode, the drain electrode and the channel with an inorganic material or organic material having low permeability for moisture and light. In addition, when the channel is formed from a carbon nanotube, the characteristics of the channel are greatly affected particularly by moisture. For this reason, a passivation film such as a silicon nitride film or hafnium oxide film may be formed at least on the channel, and the film may be covered with inorganic or organic material.

Furthermore, the field-effect transistor has a reaction field that functions as a gate electrode, on the semiconductor substrate. The reaction field may be positioned on the surface where the source electrode, the drain electrode and the channel are arranged, or may also be positioned on the surface of the semiconductor substrate remote from the source electrode, the drain electrode and the channel. It is preferable that the insulating film is provided also on the surface of the reaction field.

It is necessary to apply a desired potential (scanning potential or reference potential) to the reaction field which has been formed on the semiconductor substrate. For this reason, a gate electrode is preferably arranged around a part or all of the perimeter of the reaction field. The material of the gate electrode is not limited in particular, and may be a metal such as gold, platinum, titanium or aluminum, conductive plastic or the like.

The reaction field has target recognition molecules immobilized on its surface or is configured to be capable of immobilizing the recognition molecules on its surface. Examples of the target recognition molecules include proteins such as antibodies, enzymes and lectin; nucleic acids; and oligosaccharides or polysaccharides; or substances having any of the structures thereof. A molecule which specifically reacts with a detection target is appropriately selected. The detection target is, for example, a protein or chemical substance of particular type.

When the target recognition molecules are immobilized on the surface of the reaction field, the reaction field may be preferably moisturized so as to avoid degradation of the immobilized molecules. This is because the target recognition molecules generally tend to degrade due to dryness. In order to moisturize the reaction field, a moisturizing seal may be arranged so as to cover the reaction field. The moisturizing seal refers to a film member which is hard to allow moisture to pass through it and which is applied so as to cover the reaction field with a peelable adhesive. The film which is hard to allow moisture to pass through it is, for instance, a multilayer film having a metal layer.

On the other hand, when the reaction field is so configured as to be capable of immobilizing target recognition molecules on its surface as needed rather than having them immobilized on its surface, it is preferable that the target recognition molecules are sealed together with the biosensor chip in the packing body. The target recognition molecules which are sealed in the packing body are sealed preferably by a separate packing material. This is because, as described above, it is preferable that the field-effect transistor does not come in contact with moisture, but on the other hand, it is often the case that the target recognition molecules are preferably kept in a moisturized environment.

In order for the target recognition molecules to be capable of being immobilized on the surface of the reaction field as needed, the surface of the reaction field may be subjected, for instance, to a silanizing treatment. The silanizing treatment includes surface treatment by a silane coupling agent or other agent. The reaction field may have a self-assembly monolayer (SAM) film formed on its surface. In order to form the SAM film, firstly, a metal thin film (e.g., gold or platinum thin film) may be formed on the surface of the reaction field, followed by arrangement of the SAM film on the metal thin film.

The biosensor chip of the first form has a mounting board on which a field-effect transistor is mounted. It is preferable that the mounting board is made of an insulating material and does not have optical transparency. This is because when light which has passed through the mounting board strikes the channel or semiconductor substrate of the field-effect transistor, their characteristics change. The mounting board may be, for instance, a molded article of an organic resin containing a pigment.

The mounting board has terminals which are electrically connected to the source electrode, the drain electrode and the gate electrode of the field-effect transistor, respectively. The biosensor chip of the first form is attached to a detection device (later described) through these terminals.

The biosensor chip of the first form can be manufactured according, for instance, to the following process.

1) An insulating film such as a silicon oxide film, a silicon nitride film or a hafnium oxide film is formed on the surface of a semiconductor substrate. The insulating film may be formed by, for example, thermal oxidation method or CVD.

2) A source electrode, a drain electrode and a channel which connects the electrodes are formed on the insulating film. In the case of a carbon nanotube channel, the channel is formed by CVD using an organic material such as ethyl alcohol, or using a ready-made carbon nanotube. In the case of polysilicon channel or amorphous silicon channel, the channel can be formed by CVD, epitaxial growth or other method. After channel formation, a passivation film formed of an insulating film such as a silicon oxide film, a silicon nitride film and or hafnium oxide film is formed at least on the channel, and both ends of the channel are opened. After that, a conductive material is deposited by sputtering or other method on the insulating film so as to be connected with the ends of the channel, and unnecessary portions are removed by etching to form the source electrode and the drain electrode.

3) A reaction field is formed on the semiconductor substrate. In the case of the first form, the reaction field is formed on the surface where the source electrode, the drain electrode and the channel are formed, in a desired region on the insulating film which has been formed in the above step (1). The reaction field is subjected to surface treatment such that target recognition molecules can be immobilized on the reaction field. The surface treatment differs between in-liquid measurement and in-air measurement. When the biosensor is used for in-liquid measurement, a metal film such as a gold or platinum film, which is chemically stable, is formed b vacuum deposition, sputtering or other method in order to limit the generation of ions from the liquid sample. After that, an SAM film is formed so as to facilitate the immobilization of target recognition molecules. When the biosensor is used for in-air measurement, the surface is treated with a silane coupling agent or other agent. Furthermore, a scanning electrode or a reference electrode is arranged around the perimeter or in the vicinity of the reaction field so that a desired potential can be applied to the reaction field. This scanning electrode or reference electrode is formed, for example, simultaneously with the source, electrode and the drain electrode in the step 2).

4) The semiconductor substrate including the field-effect transistor is mounted on the mounting board to form the biosensor chip. The mounting board has three external connection terminals formed thereon. The respective terminals of the mounting board are connected to the source electrode, the drain electrode and the gate electrode of the field-effect transistor by, for example, wire bonding or bump connection method.

5) The source electrode, the drain electrode, the channel and the connections of the terminals are sealed by an inorganic material or an organic material having low permeability for moisture and light by, for example, potting method or transfer molding. In order to prevent the peeling of the sealing material, the biosensor chip may be subjected to plasma cleaning treatment before the sealing treatment. However, when the carbon nanotube is used in the field-effect transistor, there is a high possibility that the carbon nanotube is destroyed by plasma, and accordingly a shield layer formed of a metal is provided on the carbon nanotube, for instance. Thereby, the destruction due to the plasma can be prevented.

The biosensor kit is obtained by sealing the biosensor chip thus obtained in the above described step 5), in a packing body provided with a desiccating agent or a moisture absorbent. When the target recognition molecules are immobilized on the biosensor chip beforehand, the reaction field is covered with a moisturizing seal. In addition, when the target recognition molecules are not immobilized on the biosensor chip beforehand, the target recognition molecules, which have been separately packed, are enclosed in the packing body. It should be noted that the packing body may be filled with an inert gas.

Figure 1B:
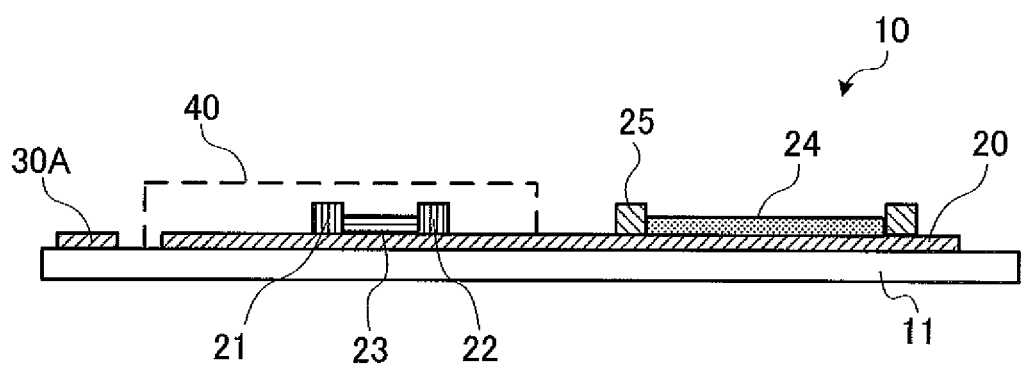
FIG. 1B is a sectional view of the biosensor chip taken along line A-A' illustrated in FIG. 1A.

FIG. 1 illustrates a first example of a biosensor chip of a first form. FIG. 1A is a plan view of biosensor chip 10, and FIG. 1B is a sectional view of biosensor chip 10 taken along line A-A' of FIG. 1A. Biosensor chip 10 illustrated in FIG. 1 has mounting board 11; and components constituting a field-effect transistor: semiconductor substrate 20, source electrode 21, drain electrode 22, channel 23, reaction field 24, and scanning electrode or reference electrode 25. Furthermore, three external connection terminals 30 (30A, 30B, 30C) are arranged at one end of the mounting board 11, and are electrically connected to source electrode 21, drain electrode 22, and scanning electrode or reference electrode 25, respectively.

It is preferable to seal source electrode 21, drain electrode 22 and channel 23 of the biosensor chip 10 with sealing member 40, to shield light. Sealing member 40 may be a member which does not allow light to pass through it, and may be made of organic resin or inorganic material. It should be noted that at least channel 23 of biosensor chip 10 is covered with a passivation film (not shown).

Figure 2A:
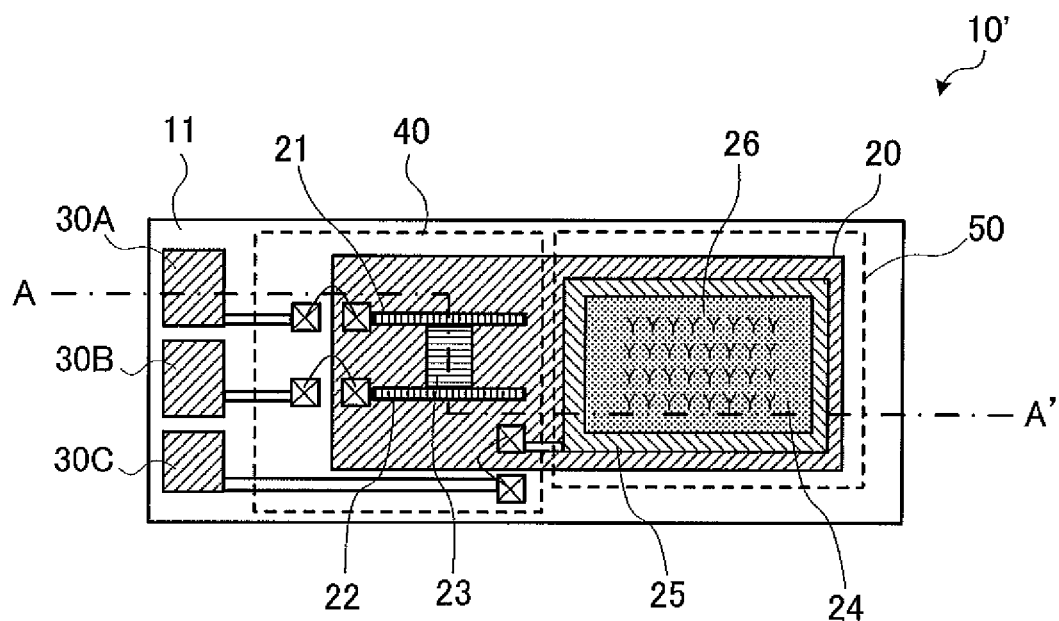
FIG. 2A is a plan view of a second example of the biosensor chip of the first form.
Figure 2B:
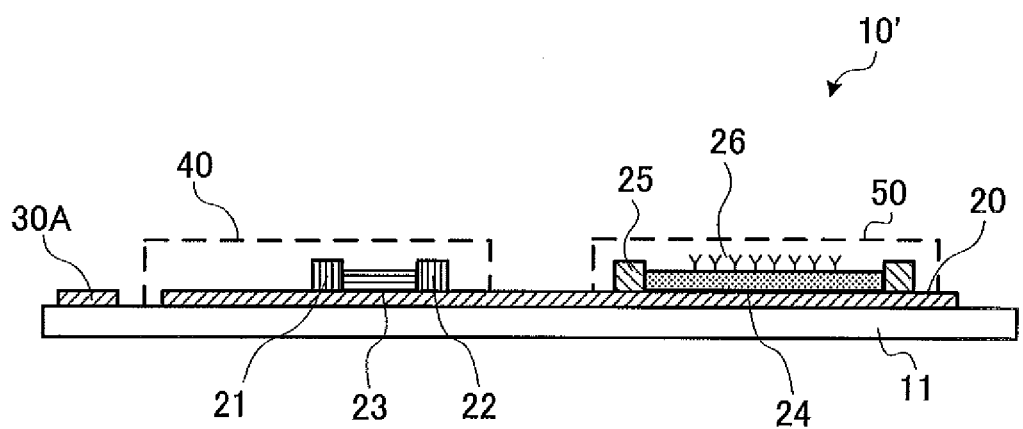
FIG. 2B is a sectional view of the biosensor chip taken along line A-A' illustrated in FIG. 2A.

FIG. 2 illustrates a second example of the biosensor chip of the first form. FIG. 2A is a plan view of biosensor chip 10', and FIG. 1B is a sectional view of biosensor chip 10' taken along line A-A' of FIG. 2A. Biosensor chip 10' illustrated in FIG. 2 includes components similar to those of biosensor chip 10 illustrated in FIG. 1, and furthermore, target recognition molecules 26 are immobilized on reaction field 24. Moreover, reaction field 24 of biosensor chip 10' is covered and moisturized with moisturizing seal 50.

Figure 3A:
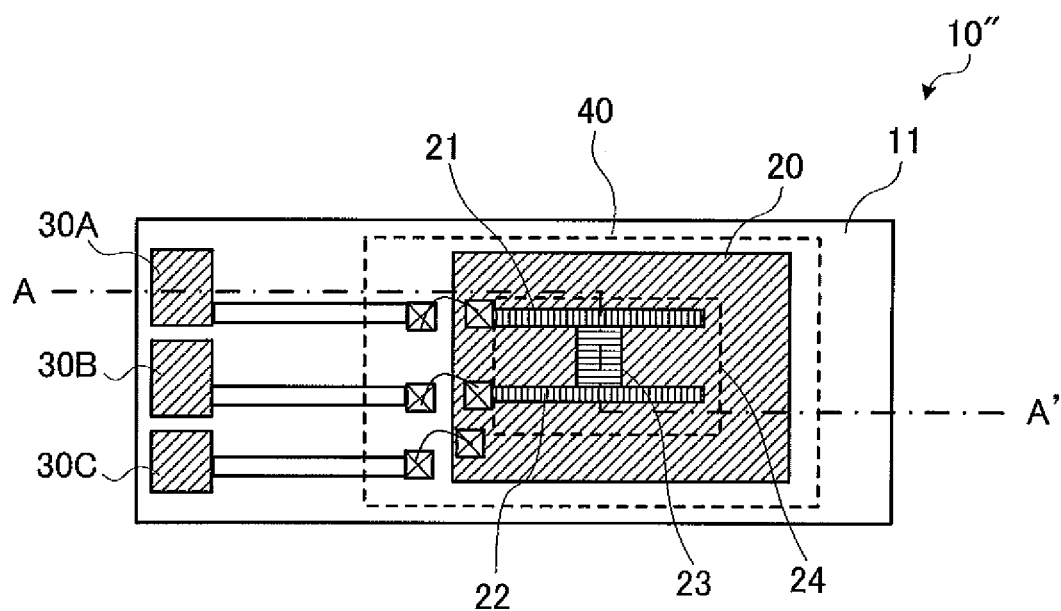
FIG. 3A is a plan view of a third example of the biosensor chip of the first form.
Figure 3B:
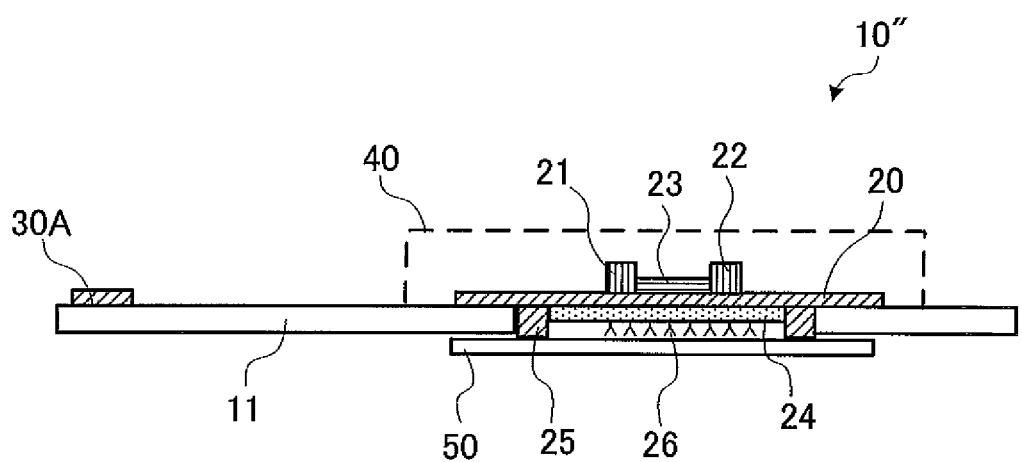
FIG. 3B is a sectional view of the biosensor chip taken along line A-A' illustrated in FIG. 3A.

FIG. 3 illustrates a third example of the biosensor chip of the first form. FIG. 3A is a plan view of biosensor chip 10", and FIG. 3B is a sectional view of biosensor chip 10" taken along line A-A' of FIG. 3A. Biosensor chip 10" includes components similar to those of biosensor chip 10' illustrated in FIG. 2, but reaction field 24 is provided on the back surface of the semiconductor substrate 20 (i.e., surface remote from the surface on which source electrode 21, drain electrode 22 and channel 23 are arranged). Reaction field 24 of biosensor chip 10" has target recognition molecules 26 immobilized thereon, and has moisturizing seal 50 arranged thereon. It should be noted that as with biosensor chip 10, reaction field 24 may not have target recognition molecules 26 immobilized thereon, and may not have moisturizing seal 50 arranged thereon.

Figure 4A:
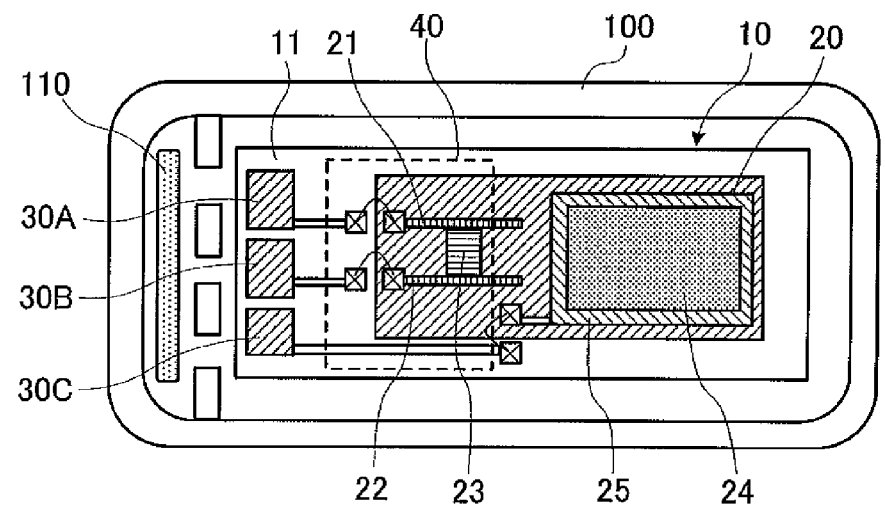
FIG. 4A is a plan view of a biosensor kit including the biosensor chip illustrated in FIG. 1.
Figure 4B:
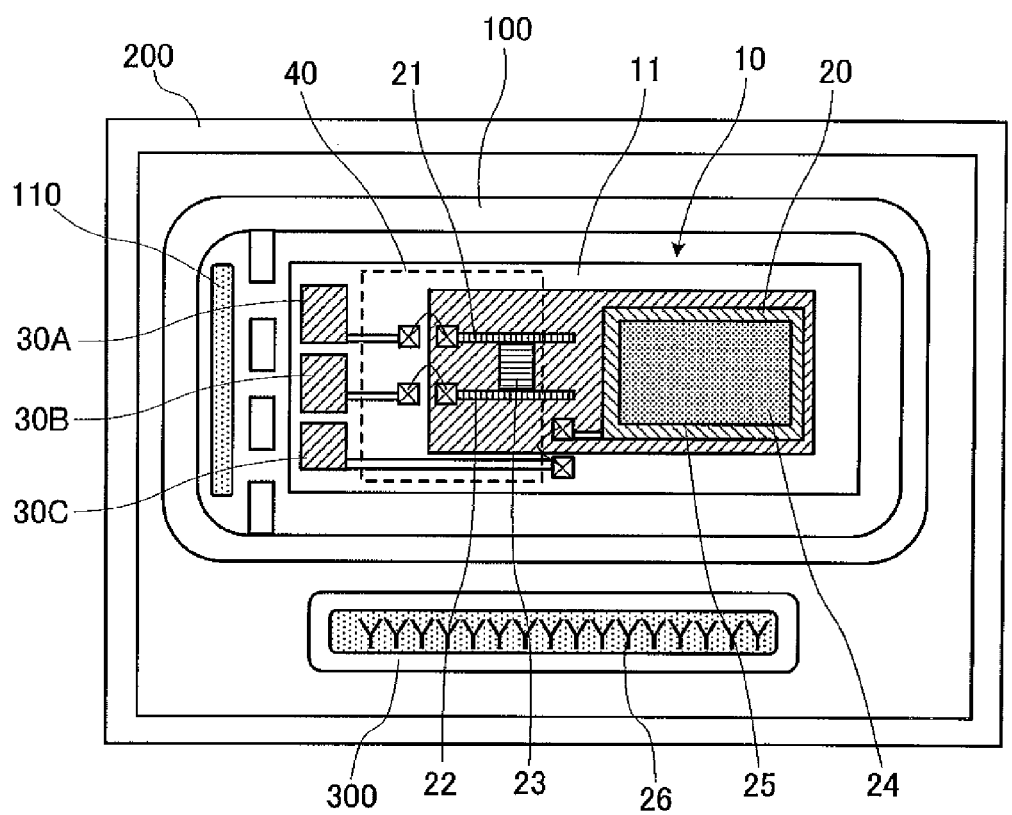
FIG. 4B is a plan view of a biosensor kit including the biosensor chip illustrated in FIG. 1.

FIG. 4A illustrates a biosensor kit which has biosensor chip 10 (see FIG. 1) sealed in chip packing body 100. The moisture absorbent or desiccating agent 110 is also sealed in chip packing body 100 together with biosensor chip 10. FIG. 4B illustrates a biosensor kit which has biosensor chip 10 and target recognition molecules 26 sealed in kit packing body 200. The biosensor chip is sealed in packing body 100, as illustrated in FIG. 4A. Target recognition molecules 26 are sealed also in separate packing body 300.

Figure 5:
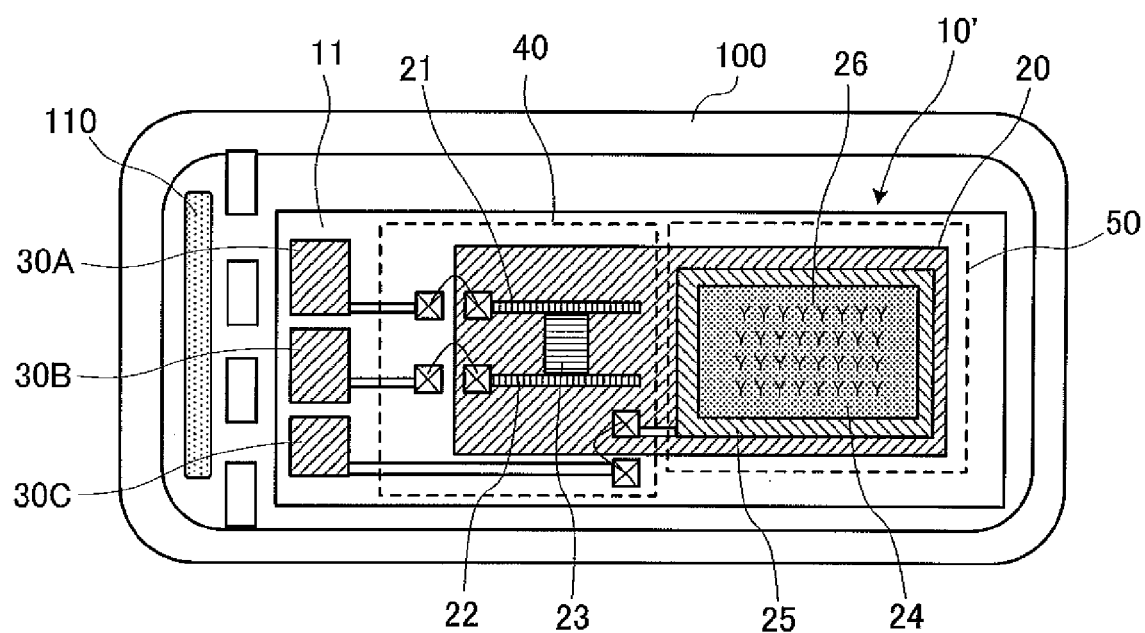
FIG. 5 is a plan view of a biosensor kit including the biosensor chip illustrated in FIG. 2.

FIG. 5 illustrates a biosensor kit which has biosensor chip 10' (FIG. 2) sealed in chip packing body 100. The moisture absorbent or desiccating agent 110 is sealed in chip packing body 100 together with biosensor chip 10'.

Figure 6:
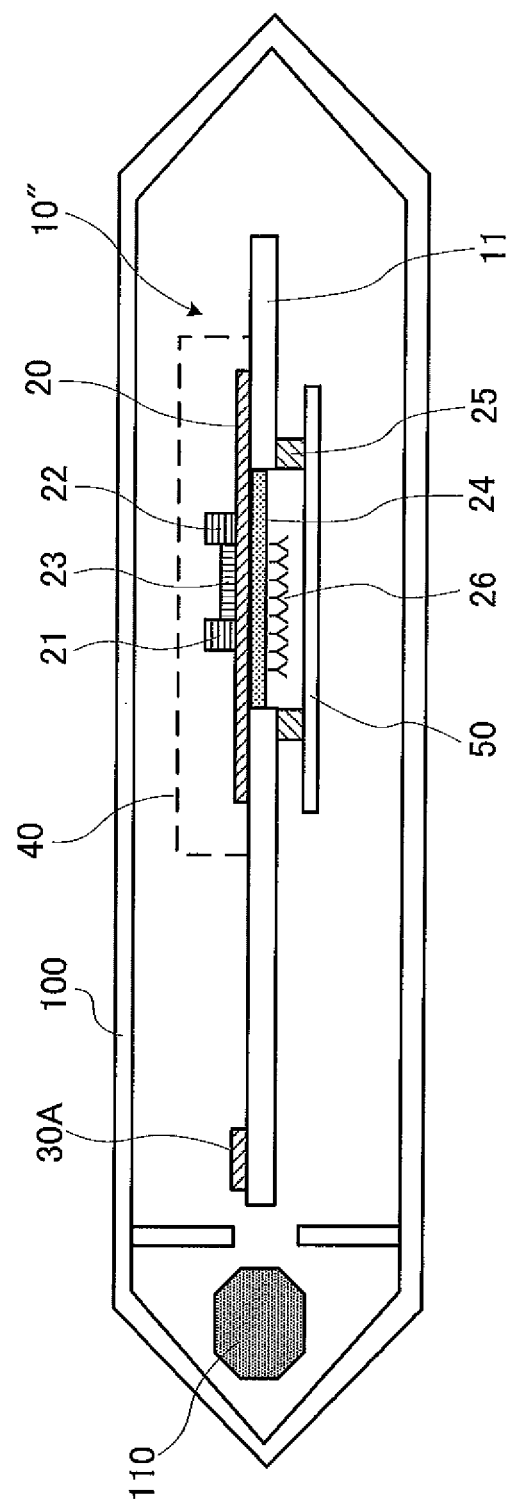
FIG. 6 is a sectional view of a biosensor kit including the biosensor chip illustrated in FIG. 3.

FIG. 6 illustrates a biosensor kit which has biosensor chip 10" (FIG. 3) sealed in chip packing body 100. The moisture absorbent or desiccating agent 110 is sealed in chip packing body 100 together with biosensor chip 10".

Figure 7:
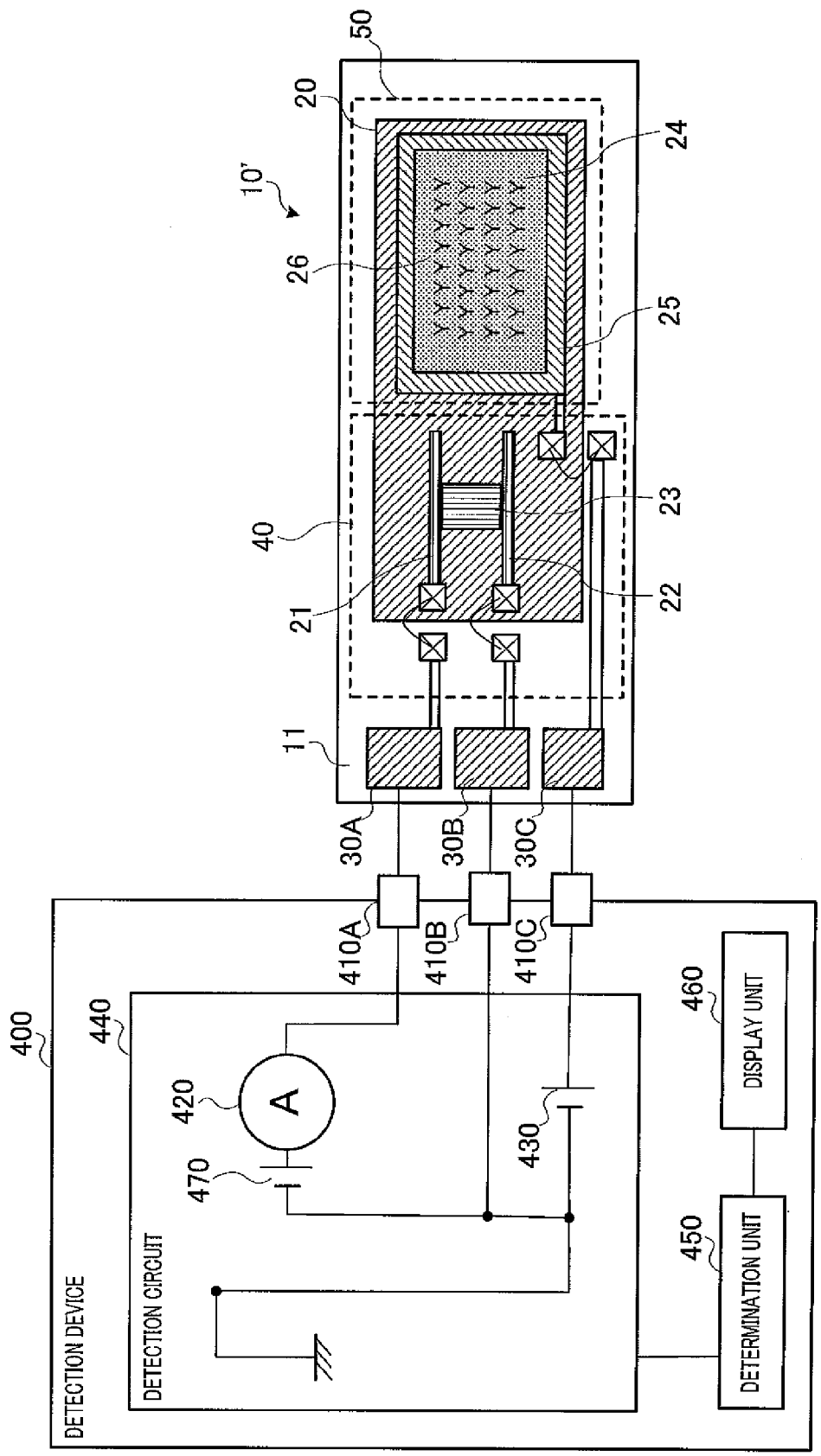
FIG. 7 is a plan view of a detection system having the biosensor chip illustrated in FIG. 2.

FIG. 7 illustrates a detection system which includes the biosensor chip of the first form (biosensor chip 10' (see FIG. 2) as an example), and detection device 400. Detection device 400 includes detection circuit 440 which includes: three input terminals 410 (410A to 410C); electric current detection unit 420 connected to input terminal 410A; power source 470 connected to electric current detection unit 420; a ground connected to input terminal 410B; and power source 430 connected to input terminal 410C. Detection device 400 further includes: determination unit 450 for determining a detection result on the basis of the detected electric current; display unit 460 for displaying the result; and storage unit for recording the result (not shown). Determination unit 450 includes a processor, a ROM, a RAM and the like which are necessary for performing calculation on the basis of the detected electric current value, and determining the presence or absence of and the concentration of the detection target. A liquid crystal display, an organic EL display, a plasma display or the like is used as display unit 460. A lamp indicator with an LED may be used as a simple display unit. The storage unit includes a rewritable nonvolatile memory, for instance, a flash memory.

Biosensor chip 10' is attached to detection device 400, whereby input terminals 410A to 410C of the detection device are connected to external connection terminals 30A to 30C of biosensor chip 10', respectively. With this configuration, power source 430 can apply a desired potential to scanning electrode or reference electrode 25, and electric current detection unit 420 can detect the electric current flowing through channel 23.

Determination unit 450 stores therein, for instance, a relationship between the electric current to be detected and the amount of the detection target (e.g., working curve).

Biosensor Chip of Second Form

The biosensor chip of the second form has a mounting board, and a reaction field formed on the mounting board. A semiconductor substrate may be arranged on the mounting board, and the reaction field is preferably formed on the semiconductor substrate. A desired potential needs to be applied to the reaction field of the biosensor chip of the second form. For this reason, a reference electrode is arranged around a part or all of the perimeter of the reaction field.

As in the case of the biosensor chip of the first form, the reaction field has target recognition molecules immobilized on its surface, or is configured to be capable of immobilizing the recognition molecules on the surface. The reaction field may also be moisturized by a moisturizing seal or the like.

The mounting board is similar to the mounting board of the first form. An external connection terminal for applying a potential to the reference electrode of the reaction field, and an external connection terminal for taking out the potential generated in the reaction field are arranged on the mounting board. The biosensor chip of the second form is attached to a detection device (later described) through these terminals.

The biosensor chip of the second form can be manufactured, for instance, according to the following process. 1) An insulating film such as a silicon oxide film, a silicon nitride film or a hafnium oxide film is formed on the surface of a semiconductor substrate. The insulating film may be formed by thermal oxidation, CVD method or other method. 2) A reaction field is formed in a desired region of the semiconductor substrate having the insulating film formed thereon in the above step 1). Next, a part of the insulating film is opened in which an electrode for drawing the potential of the reaction field is to be formed. Next, a conductive film made of aluminum or other metal is formed on the insulating film around the perimeter or in the vicinity of this reaction field. Then, a gate electrode or a reference electrode; an interconnection drawn from the electrode; a connection terminal for being connected to an interconnection on the mounting board (later described); and an electrode for drawing the potential of the reaction field are formed by etching. The reaction field formed in this way is subjected to surface treatment such that target recognition molecules can be immobilized thereon, similarly to that of the first form. Furthermore, the target recognition molecules may be immobilized on the reaction field.

3) The semiconductor substrate having the reaction field thereon is mounted on the mounting board to form the biosensor chip. The mounting board has two external connection terminals formed thereon. One of the external connection terminals is connected to a terminal to be connected to the gate electrode of an external field-effect transistor, and the other is connected to a terminal of the scanning electrode or reference electrode, by wire bonding or bump connection method, for instance. The connecting portions of the external connection terminals are sealed by an inorganic material or an organic material having low permeability for moisture, by potting method or transfer molding, for instance.

The biosensor kit is obtained by sealing the obtained biosensor chip in the packing body.

It should be noted that a substrate to be used in the biosensor chip of the present form is not limited to the semiconductor substrate, but can be an insulating substrate. When a glass substrate is used, for instance, the biosensor chip can be prepared without separately preparing the mounting board. Firstly, a conductive film made of aluminum or other metal is formed on the glass substrate, and a reaction field, an interconnection drawn from the reaction field, and an external connection terminal are formed by etching. Next, an insulating film such as a silicon oxide film, a silicon nitride film or a hafnium oxide film is formed by CVD so as to cover the reaction field. Next, the conductive film made of aluminum or other metal is formed on the insulating film around the perimeter or in vicinity of the reaction field, and a scanning electrode or reference electrode, an interconnection drawn from the electrode and an external connection terminal are formed by etching. The biosensor kit is obtained by subjecting the reaction field obtained in this way to a surface treatment similar to that described above, and sealing the reaction field in the packing body.

Figure 8A:
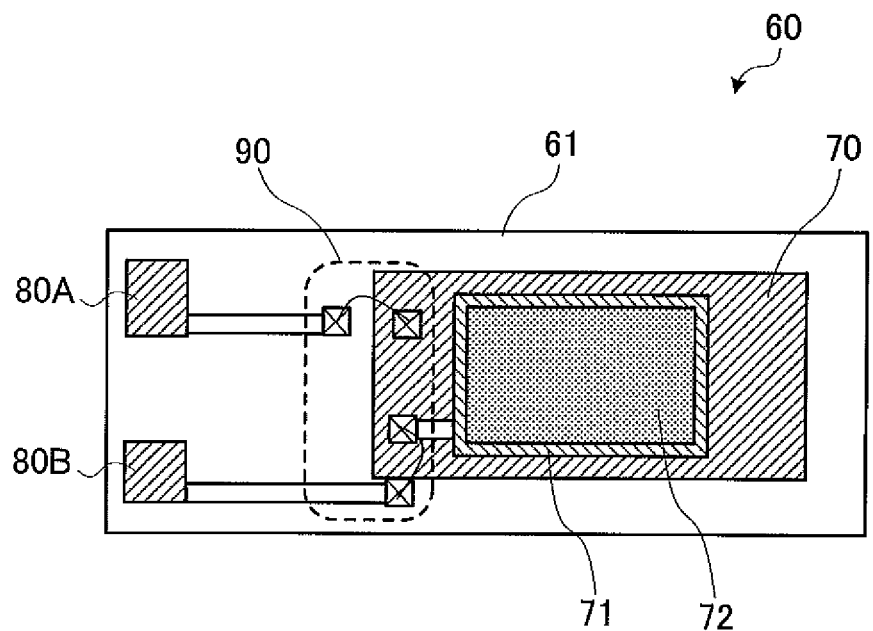
FIG. 8A is a plan view of an example of a biosensor chip of a second form.

FIG. 8A illustrates an example of a biosensor chip of a second form. Biosensor chip 60 has mounting board 61, and semiconductor substrate 70 arranged on mounting board 61. Semiconductor substrate 70 has reference electrode 71 and reaction field 72 arranged thereon. Mounting board 61 has two external connection terminals 80 (external connection terminal 80A for applying gate potential, and external connection terminal 80B for applying reference potential) arranged thereon. A connector portion may be sealed by arranging sealing member 90 thereon.

Figure 8B:
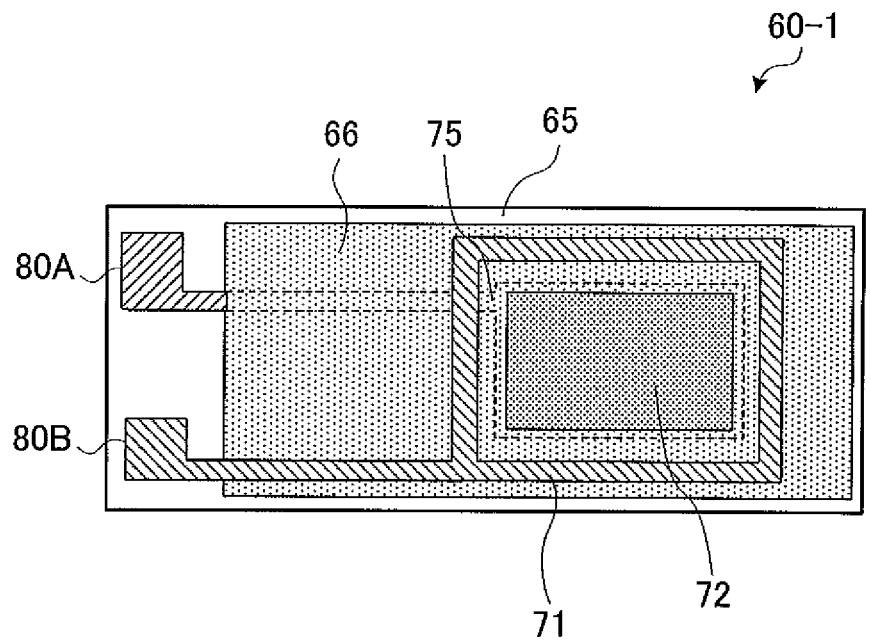
FIG. 8B is a plan view of another example of the biosensor chip of the second form.

FIG. 8B illustrates another example of the biosensor chip of the second form which includes a glass substrate. Biosensor chip 60-1 has glass substrate 65; reaction field 72 and interconnection 75 for drawing a potential in the reaction field, which are formed on the glass substrate; insulating film 66 formed thereon; and reference electrode 71 and an interconnection for applying a reference potential, which are formed on the insulating film. Glass substrate 65 further has two external connection terminals (external connection terminal 80A for drawing gate potential, and external connection terminal 80B for applying reference potential) arranged thereon.

Figure 9A:
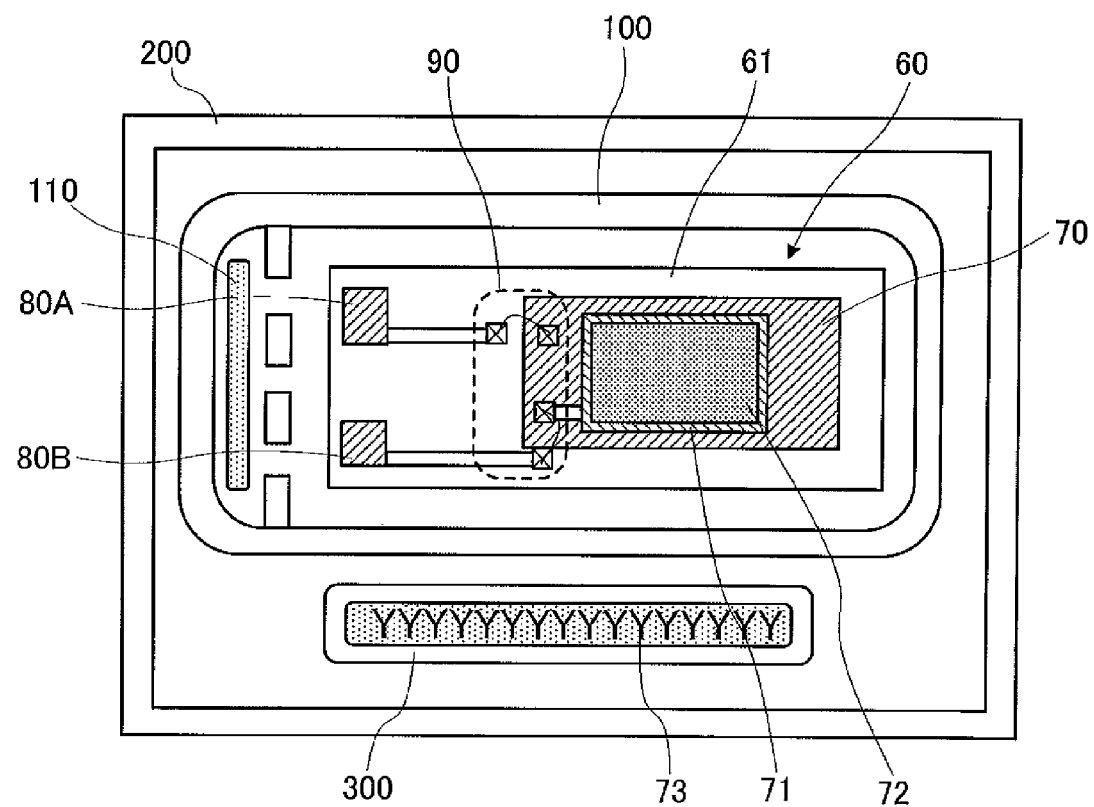
FIG. 9A is a plan view of a biosensor kit including a biosensor chip illustrated in FIG. 8A.

FIG. 9A illustrates a biosensor kit including kit packing body 200 that encloses therein biosensor chip 60 sealed in chip packing body 100, and target recognition molecules 73 which are sealed in packing body 300. Moisture absorbent 110 is also sealed together with biosensor chip 60 in chip packing body 100.

Figure 9B:
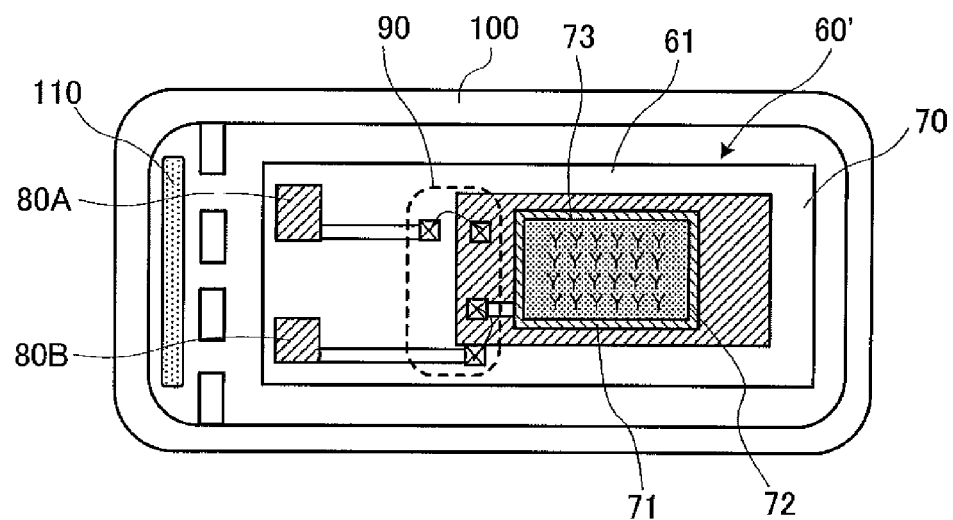
FIG. 9B is a plan view of a biosensor kit including the biosensor chip illustrated in FIG. 8A.

FIG. 9B illustrates a biosensor kit that has biosensor chip 60' in which target recognition molecules 73 are immobilized on the reaction field 72 of biosensor chip 60 illustrated in FIG. 8 and the reaction field is covered with moisturizing seal (not shown), sealed in chip packing body 100. Moisture absorbent 110 is also sealed in chip packing body 100 together with biosensor chip 60'

Figure 10:
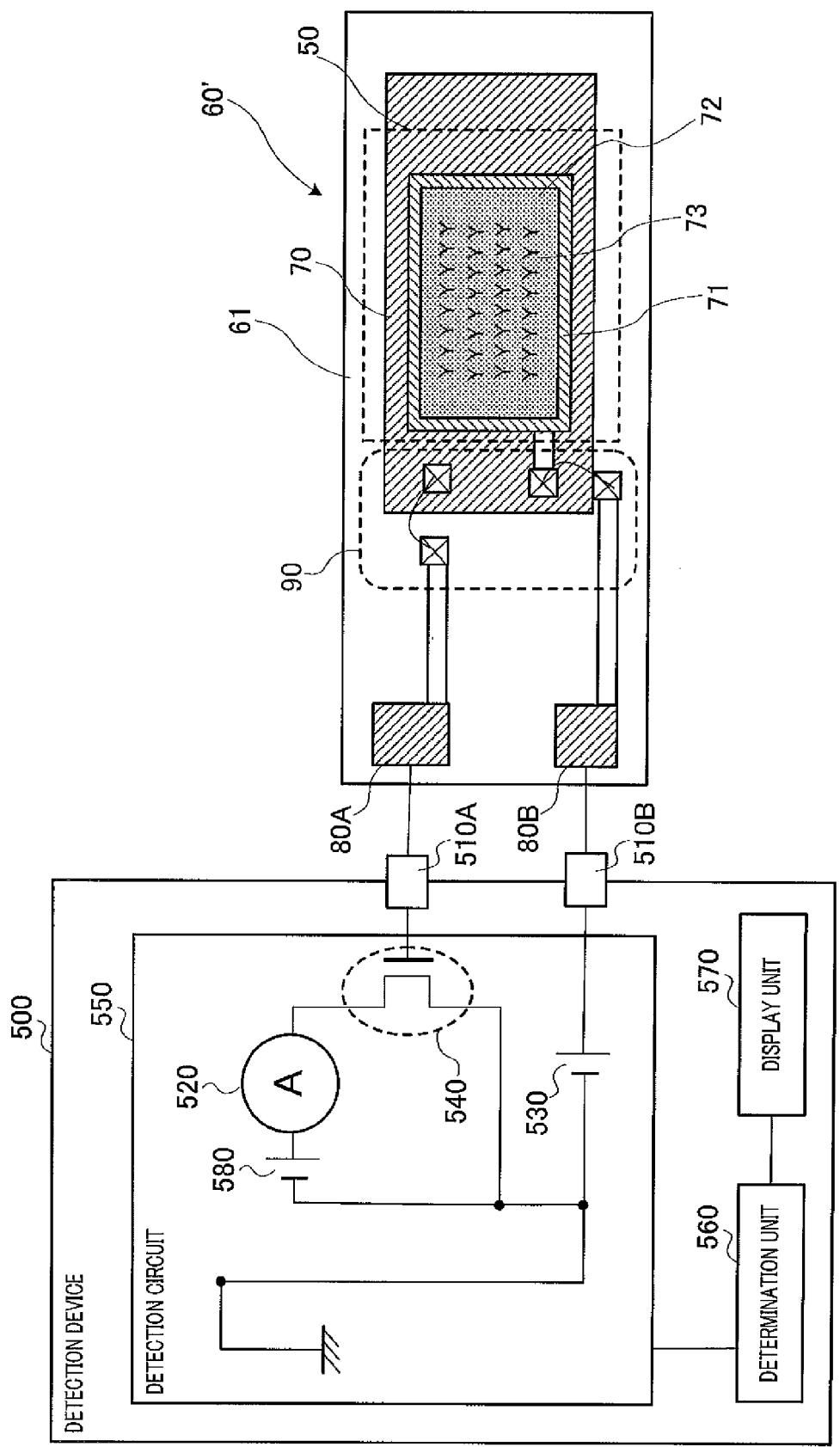
FIG. 10 is a plan view of a detection system having the biosensor chip illustrated in FIG. 9B.

FIG. 10 illustrates a detection system for a detection target, which has biosensor chip 60' (see FIG. 9B) of the second form attached to detection device 500. Detection device 500 has detection circuit 550 which includes: two input terminals 510 (510A, 510B); field-effect transistor 540; electric current detection unit 520; power source 580; and power source 530. Input terminal 510A is connected to the gate of field-effect transistor 540. Input terminal 510B is connected to power source 530. Detection device 500 further includes: determination unit 560 for determining a detection result on the basis of the detected electric current; display unit 570 for displaying the result; and a storage unit for recording the result (not shown). Determination unit 560 includes a processor, a ROM, a RAM and the like which are necessary for performing calculation on the basis of the detected electric current value, and determining the presence or absence of and the concentration of the substance to be detected. A liquid crystal display, an organic EL display, a plasma display or the like is used as display unit 570. A lamp indicator with an LED may be used as a simple display unit. The storage unit includes a rewritable nonvolatile memory, for instance, a flash memory. Field-effect transistor 540 includes: a channel which is formed, for instance, from a carbon nanotube, polysilicon and amorphous silicon; a source electrode; and a drain electrode. These components are sealed by an inorganic material or an organic material having low permeability for moisture and light. With this configuration in which field-effect transistor 540 is provided in detection device 500, it is only necessary to prepare high-sensitivity field-effect transistors in a number equal to that of detection devices. Thereby, the influence of yield can be mitigated. In addition, the biosensor chip itself can be inexpensively manufactured.

Biosensor chip 60' is attached to detection device 500, and input terminals 510A and 510B of the detection device are connected to external connection terminals 80A and 80B of biosensor chip 60', respectively. Thereby, the potential generated in reaction field 72 can be used as a gate potential of field-effect transistor 540, and power source 530 can apply a desired reference potential to reference electrode 71.

Determination unit 570 stores therein, for instance, a relationship between the electric current to be detected and the amount of the detection target (e.g., working curve).

Method for Detecting Detection Target

A detection target can be detected using the biosensor kit of the present invention according to the following procedure, for example.

Firstly, the biosensor chip is taken out from the packing body of the biosensor kit of the present invention. When the taken out reaction field of the biosensor chip does not have any target recognition molecules immobilized thereon, the target recognition molecules are immobilized.

Next, a sample containing the detection target is added to the reaction field. The sample is usually an aqueous solution. After the sample has been added to the reaction field, the sample is incubated. Then, the reaction field is washed. The reaction field may be washed, for instance, with water. After the reaction field has been washed, the washing liquid (water) in the reaction field is preferably removed as much as possible. The washing liquid can be removed, for instance, by drying the reaction field under reduced pressure, or drying the reaction field by blowing a gas to the reaction field.

After that, the biosensor chip is attached to the above detection device. After attachment, an electric current flowing through the channel of the field-effect transistor (which may be provided in biosensor chip or detection device) is measured. The presence or absence of and the concentration of the detection target in the sample are detected on the basis of the measurement result.

The present application claims the priority of Japanese Patent Application No. 2010-064676 filed on March 19 in 2010, the contents of which including the specification and drawings are incorporated herein by reference in its entirety.

Industrial Applicability

The present invention can achieve practical high-sensitivity biosensing by avoiding the degradation of a PET-based biosensor during the storage of transportation of the biosensor.

REFERENCE SIGNS LIST 10, 10' and 10" Biosensor chip
11 Mounting board
20 Semiconductor substrate
21 Source electrode
22 Drain electrode
23 Channel
24 Reaction field
25 Scanning electrode or reference electrode
26 Target recognition molecules
30A, 30B and 30C External connection terminal
40 Sealing member
50 Moisturizing seal
60, 60' and 60-1 Biosensor chip
61 Mounting board
65 Glass substrate
66 Insulating film
70 Semiconductor substrate
71 Reference electrode
72 Reaction field
73 Target recognition molecules
75 Interconnection for drawing potential of reaction field
80A and 80B External connection terminal
90 Sealing member
91 Moisturizing seal
100 Chip packing body
110 Moisture absorbent or desiccating agent
200 Kit packing body
300 Packing body
400 Detection device
410A, 410B and 410C Input terminal
420 Electric current detection unit
430 Power source
440 Detection circuit
450 Determination unit
460 Display unit
470 Power source
500 Detection device
510A and 510B Input terminal
520 Electric current detection unit
530 Power source
540 Field-effect transistor
550 Detection circuit
560 Determination unit
570 Display unit
580 Power source

The invention claimed is:

1. A biosensor kit comprising:
a biosensor chip for measuring a value of an electric current in a field-effect transistor, the electric current generated when a detection target is allowed to react with a target recognition molecule immobilized onto a reaction field connected to the field-effect transistor; and
a packing body which seals therein the biosensor chip and a desiccating agent, the packaging body being formed from a packing material having a metal film, wherein
the biosensor chip has a mounting board, the field-effect transistor mounted on the mounting board, the reaction field formed on the mounting board for applying a gate potential to the field-effect transistor, and the target recognition molecule immobilized on the reaction field,
the mounting board includes a first external connection terminal connected to a source electrode of the field-effect transistor, a second external connection terminal connected to a drain electrode of the field-effect transistor, and a third external connection terminal for applying a predetermined potential to the reaction field, and
the reaction field on which the target recognition molecule immobilized is moisturized by a moisturizing member in the packing body sealing therein with the desiccating agent.

2. The biosensor kit according to claim 1, wherein the reaction field has been subjected to surface treatment for immobilizing the target recognition molecule onto the reaction field.

3. The biosensor kit according to claim 2, wherein the surface treatment for the reaction field is silanizing treatment.

4. The biosensor kit according to claim 2, wherein the surface treatment for the reaction field is a treatment in which a thin film of gold or platinum is formed on the reaction field and an SAM film is formed on the thin film.

5. The biosensor kit according to claim 1, wherein the reaction field is formed on a semiconductor substrate arranged on the mounting board.

* * * * *